United States Patent
Allan

(10) Patent No.: US 9,126,922 B2
(45) Date of Patent: Sep. 8, 2015

(54) METHODS AND SYSTEMS FOR THE PRODUCTION OF DIESTERS FROM TRIACYLGLYCERIDE ESTERS

(75) Inventor: Tapsak Mark Allan, Orangeville, PA (US)

(73) Assignee: Empire Technology Development LLC, Wilmington, DE (US)

( * ) Notice: Subject to any disclaimer, the term of this patent is extended or adjusted under 35 U.S.C. 154(b) by 422 days.

(21) Appl. No.: 13/430,090

(22) Filed: Mar. 26, 2012

(65) Prior Publication Data
US 2013/0253211 A1 Sep. 26, 2013

(51) Int. Cl.
| | |
|---|---|
| C07C 59/147 | (2006.01) |
| C07C 51/00 | (2006.01) |
| C07C 51/44 | (2006.01) |
| C07C 67/475 | (2006.01) |
| C07C 67/54 | (2006.01) |
| C07C 51/353 | (2006.01) |

(52) U.S. Cl.
CPC .............. *C07C 51/44* (2013.01); *C07C 51/353* (2013.01); *C07C 67/475* (2013.01); *C07C 67/54* (2013.01)

(58) Field of Classification Search
USPC .................................................. 554/124, 121
See application file for complete search history.

(56) References Cited

U.S. PATENT DOCUMENTS

| | | | |
|---|---|---|---|
| 5,618,933 A | 4/1997 | Dordick et al. | |
| 5,872,199 A | 2/1999 | Bloembergen et al. | |
| 6,242,593 B1 | 6/2001 | Bloembergen et al. | |
| 6,384,243 B1 | 5/2002 | Brunerie | |
| 7,534,917 B1 * | 5/2009 | Ngo et al. | 562/595 |
| 7,592,002 B2 | 9/2009 | Gupta | |
| 2011/0015385 A1 | 1/2011 | Timmermans et al. | |

OTHER PUBLICATIONS

Barrett et al., Scandium(III) or lanthanide(III) triflates as recyclable catalysts for the direct acetylation of alcohols with acetic acid, *Chem Commun* (1997), 351-352 (Abstract).

Boenig, Unsaturated Polyesters: Structures and Properties; Chapter 6, Effect of Structure of the Polyester Backbone on Properties of the Cured Products, Elsevier Publishing Company, Amsterdam, London & New York (1964), pp. 55-135.

Brunow et al., A Synthesis of (Z)-Octadec-9-enedioic Acid, *Australian Journal of Chemistry* (1995), 48(11):1893-1897 (Abstract).

Chakraborti et al., Protic Acid Immobilized on Solid Support as an Extremely Efficient Recyclable Catalyst System for a Direct and Atom Economical Esterification of Carboxylic Acids with Alcohols, *J Org Chem* (Jul. 21, 2009), 74(16):5967-5974 (Abstract).

(Continued)

*Primary Examiner* — Deborah D Carr
(74) *Attorney, Agent, or Firm* — Pepper Hamilton LLP

(57) ABSTRACT

Efficient methods for the production of long-chain unsaturated dicarboxylic compounds are disclosed. Unsaturated dicarboxylic compounds may be prepared from a reaction mixture containing unsaturated carboxylic compounds in the presence of one or more catalysts. In addition to the unsaturated dicarboxylic compounds, alkene compounds may also be produced. The alkene compounds may be removed from the reaction mixture under reduced pressure. The method may also use a wiped-film still as a means to remove the alkene compounds from the reaction mixture. Reaction conditions may be monitored and/or controlled through the use of one or more electronic system(s) in communication with a variety of sensors and controllable devices.

33 Claims, 5 Drawing Sheets

(56) References Cited

OTHER PUBLICATIONS

Chen et al., Direct Atom-Efficient Esterification between Carboxylic Acids and Alcohols Catalyzed by Amphoteric, Water-Tolerant TiO(acac)$_2$, *J Org Chem* (Oct. 14, 2005), 70(21):8625-8627 (Abstract).

Gouw et al., Efficiency Measurements on an All-Glass Wiped-Film Still, *Ind. Eng. Chem. Process Des. Dev.* (Jan. 1967), 6(1):62-67 (Abstract).

Ishihara et al., Direct ester condensation from a 1:1 mixture of carboxylic acids and alcohols catalyzed by hafnium(IV) or zirconium(IV) salts, *Tetrahedron* (Mar. 22, 2002), 58:8179-8188.

Ishihara et al., Bulky DiarylammoniumArenesulfonates as Selective Esterification Catalysts, *J Am Chem Soc* (Mar. 30, 2005), 127(12):4168-4169 (Abstract).

Komura et al., FeCl$_3$-6H$_2$O as a Versatile Catalyst for the Esterification of Steroid Alcohols with Fatty Acids, *Synthesis* (May 19, 2008), 21:3407-3410 (Abstract).

Lu et al., Soybean oil-based, aqueous cationic polyurethane dispersions: Synthesis and properties, *Process in Organic Coatings* (Sep. 2010), 69(1):31-37 (Abstract).

McFadden et al., Synthesis of Vegetable Oil-Based Step-Growth Polymers Using a 2"Wiped-Film Still, *Department of Chemistry, Bloomsburg University, Pennsylvania* (241$^{st}$ ACS National Meeting & Exposition, Anaheim, CA, Mar. 27-31, 2011).

Moumne et al., Efficient Synthesis of β2-Amino Acid by Homologation of α$^2$-Amino Acids Involving the Reformatsky Reaction and Mannich-Type Imminium Electrophile, *J Org Chem* (Apr. 14, 2006), 71(8):3332-3334 (Abstract).

Sharghi et al., Al$_2$O$_3$/MeSO$_3$H (AMA) as a new reagent with high selective ability for monoesterification of diols, *Organic Chemistry* (2003), 59:3627-3633 (Abstract).

Srinivas et al., Silica Chloride: A Versatile Heterogeneous Catalyst for Esterification and Transesterification, *Synthesis* (Jul. 10, 2003), 16:2479-2482 (Abstract).

Warwel et al., Polyesters by lipase-catalyzed polycondensation of unsaturated and epoxidized long-chain, α,ω-dicarboxylic acid methyl esters with diols, *Journal of Polymer Science Part A: Polymer Chemistry* (Mar. 27, 2001), 39(10):1601-1609 (Abstract).

Warwel, Polyesters of ω-Unsaturated Fatty Acid Derivatives, *Macromol Chem Phys* (2001), 202:1114-1121.

Wiped Film Evaporators, Pfaudler Reactor Systems, Equipment and Accessories (printed from internet Jan. 17, 2012).

General Description of Thin Film Distillation, SMS (printed from internet Jan. 17, 2012).

\* cited by examiner

METHODS AND SYSTEMS FOR THE PRODUCTION OF DIESTERS FROM TRIACYLGLYCERIDE ESTERS

BACKGROUND

There is great interest in replacing petroleum-based chemicals with bio-derived feedstocks, thereby producing "green" products. Such products may take advantage of renewable resources, as well as decrease manufacturing reliance on petrochemicals. Examples of green products may include inks and adhesives, including, as an example, a soy-protein based formaldehyde-free plywood adhesive. Cost may become a large factor in determining if green compositions may be adopted in industry. It would be useful to develop methods to produce the chemical building blocks for use in step-growth polymers such as polyesters, polyamides, and polyurethanes.

Step-growth polymers can be prepared from monomers having two or more functional groups capable of reacting to form long chains or networks. The physical properties of the polymers may depend on a variety of conditions, including the amount of monomer materials used, the ratio of one monomer species to another monomer species in the preparation of copolymers, and the length of a monomer chain. Among green compositions, dicarboxylic compounds may be useful for preparing such step-growth polymers or copolymers. Dicarboxylic compounds may be obtained directly from biological feedstocks, or they may be synthesized, for example, from monocarboxylic compounds.

It is therefore desirable to develop high-yield methods to prepare dicarboxylic compounds of known and specified chain length to permit increased market penetration of bio-derived step-growth polymers and copolymers.

SUMMARY

In an embodiment, methods of preparing an unsaturated $\alpha,\omega$-dicarboxylic compound may comprise contacting at least one unsaturated carboxylic compound and at least one catalyst to form a mixture, exposing the mixture to conditions suitable to form at least one unsaturated $\alpha,\omega$-dicarboxylic compound and at least one alkene compound, and removing the alkene compound from the mixture under reduced pressure.

In another embodiment, methods of preparing a mono-unsaturated $\alpha,\omega$-dicarboxylic compound may comprise contacting a mono-unsaturated carboxylic compound and at least one metathesis catalyst to form a mixture, exposing the mixture to conditions suitable to form a mono-unsaturated $\alpha,\omega$-dicarboxylic compound and an alkene compound, and removing the alkene compound from the mixture under reduced pressure by using a wiped-film still.

DETAILED DESCRIPTION

Step-growth polymers and copolymers may be prepared from a variety of bio-derived substances including starches derived from food grade commodities such as corn. Typically, modifiers derivable from petroleum based sources, such as formaldehyde, polyvinyl alcohol, m-phenylenediamine, and triethylenetetramine, may be added to cross-link the bio-derived monomers. However, such cross-linkers may still depend upon petroleum feedstocks. Dicarboxylic compounds, derivable from biological feed-stocks, may provide one type of cross-linking material for the production of such polymers and copolymers. The usefulness of bio-derived monomeric materials for the production of plastics and other polymers may be significantly improved by providing easy and high-yield methods of their production.

The methods of producing unsaturated dicarboxylic compounds, as disclosed below, are based on the conversion of biologically derivable unsaturated carboxylic compounds to unsaturated dicarboxylic compounds. As one example, a metathesis catalyst may be used to catalyze the conversion. In a metathesis reaction, an unsaturated carboxylic compound may be converted to an unsaturated dicarboxylic compound with the additional production of alkene compounds. By removing the alkene compounds from the reaction mixture, the methods may be able to shift the reaction equilibrium to increase the production of the unsaturated dicarboxylic compound, thereby improving the reaction efficiency. In addition, the separated alkene compounds may find use in their own right as chemical feed-stocks for other purposes. For example, the alkenes may be completely hydrogenated to form lubricants or fuels. Alternatively, other function groups may be added across the carbon-carbon double bonds to produce a number of other useful compounds.

Compositions

Figure 1A:
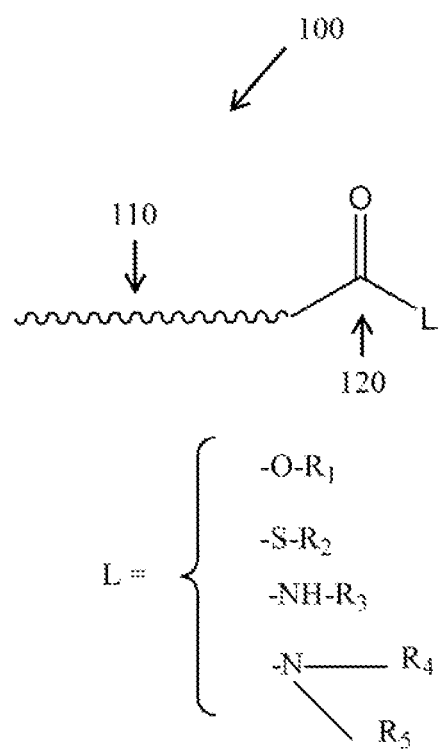
FIG. 1a illustrates a schematic of an unsaturated carboxylic compound in accordance with the present disclosure.

For the purpose of this disclosure, a "carboxylic compound" may be defined according to the structure illustrated in FIG. 1a. The carboxylic compound 100 may comprise at least a carboxyl end, 120 containing a carbonyl carbon-oxygen double bond. Further, the carboxyl end may be attached to a trailing component 110. The carboxyl end may further be conjugated to a leaving group, for example, the groups in FIG. 1a designated as L. Leaving group L may include, for example, an —O—$R_1$, an —S—$R_2$, an —NH—$R_3$, or an —N($R_4$)($R_5$) group. In some embodiments, a carboxylic compound may comprise at least a carboxyl end, in which the carboxyl end may be conjugated to a leaving group thereby forming, for example, at least an ester, a thioester, a primary amide, or a secondary amide bond.

Groups $R_1$-$R_5$ may comprise any of a number of organic substituents, including, but not limited to, aliphatic groups and aromatic groups. In one embodiment, the leaving group may include an O-aliphatic group, an O-aromatic group, an S-aliphatic group, an S-aromatic group, an N-primary amine group, or an N-secondary amine group. In one embodiment, the unsaturated carboxylic compound may be an unsaturated carboxylic acid compound. In another embodiment, the unsaturated carboxylic compound may be an unsaturated carboxylic acid ester compound. In yet another embodiment, the unsaturated carboxylic compound may be an unsaturated carboxylic acid methyl ester compound. In another embodiment, the leaving group may include a hydroxyl group, a methoxy group, an ethoxy group, a butoxy group, an isobutoxy group, a propoxy group, an isopropoxy group, a phenoxy group, a methyl sulfide group, an ethyl sulfide group, a butyl sulfide group, an isobutyl sulfide group, a propyl sulfide group, an isobutyl sulfide group, a phenyl sulfide group, a methyl amine group, an ethyl amine group, a butyl amine group, an isobutyl amine group, a propyl amine group, an isopropyl amine group, an N,N-dimethyl amine group, an N,N-di-ethyl amine group, an N,N-dibutyl amine group, an N,N-di-isobutyl amine group, an N,N-dipropyl amine group, or an N,N-di-isopropyl amine group.

The trailing component of an unsaturated carboxylic compound may include a variety of organic groups including linear chain and branched chain groups. In one embodiment, the trailing group may include a mono-unsaturated chain or a poly-unsaturated chain. In some embodiments, the liner chain may comprise "n" carbon atoms, where "n" may be an integer from about 5 to about 30. In some embodiments, "n" may be an integer from about 16 to about 22. In still another embodiment, "n" may be about 18. The integer can be an even number or an odd number. Examples of even number include 6, 8, 10, 12, 14, 16, 18, 20, 22, 24, 26, 28, 30, and ranges between any two of these values. Examples of odd numbers include 5, 7, 9, 11, 13, 15, 17, 19, 21, 23, 25, 27, 29, and ranges between any two of these values.

Figure 1B:
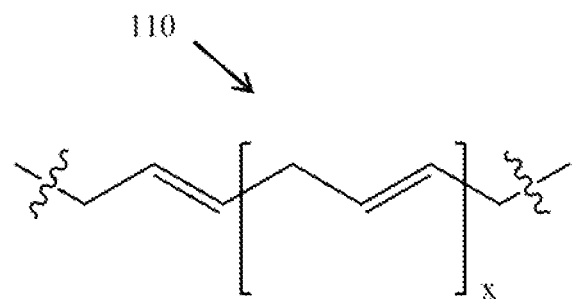
FIGS. 1b and c illustrate embodiments of components of an unsaturated carboxylic compound in accordance with the present disclosure.

FIG. 1b illustrates an embodiment of a poly-unsaturated linear chain trailing component 110 of an unsaturated carboxylic compound that may include a propenyl repeat section within the linear chain. The propenyl moiety may be repeated "x" times within the repeat section, where "x" may be an integer from 0 to 4. In some embodiments, "x" may be 0, 1, 2, 3, or 4.

The trailing component may also include lengths of straight chain alkane moieties attached at either one or both ends of the propenyl repeat section. In one embodiment, an alkane moiety may have about 1 to about 14 carbons. In another embodiment, an alkane moiety may have about 7 to about 11 carbons. In still another embodiment, an alkane moiety may have about 9 carbons. Specific examples of the number of carbons include, 1, 2, 3, 4, 5, 6, 7, 8, 9, 10, 11, 12, 13, 14, and ranges between any two of these values. It is understood that an alkane moiety attached at a first end of the propenyl repeat section may have the same number of carbons as an alkane moiety attached at the second end of the propenyl repeat section. Alternatively, the alkane moiety attached at a first end of the propenyl repeat section may have a different number of carbons than the alkane moiety attached at the second end of the propenyl repeat section.

Figure 1C:
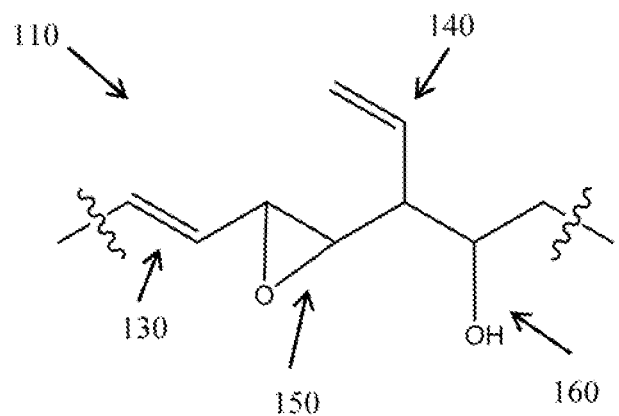

FIG. 1c illustrates another embodiment of a trailing component 110. The trailing component may include any number or distribution of unsaturated carbon-carbon bonds along a linear chain, 130. The trailing component may further include one or more functional groups including, without limitation, an epoxy group 150, an alcohol group 160, or a pendant vinyl group 140. The trailing component of a carboxylic compound may include any or all of these groups, or other functional groups.

It may be appreciated that the stereo-isomeric configuration about any one of the carbon-carbon double bonds of an unsaturated carboxylic compound may have a cis configuration or a trans configuration (or alternatively stated, E- or Z-configuration). A poly-unsaturated carboxylic compound may include cis isomers at all carbon-carbon double bonds, trans isomers at all carbon-carbon double bonds, or a combination of cis isomers at some carbon-carbon double bonds and trans isomers at the other carbon-carbon double bonds. It may further be appreciated that the unsaturated dicarboxylic compound resulting from the unsaturated carboxylic compound may similarly have any number of stereo-isomeric configurations about their carbon-carbon double bonds. An unsaturated dicarboxylic compound may have all cis configurations, all trans configurations, or a mixture of cis configurations and trans configurations about the double bonds.

In anticipation of material disclosed below, it may be appreciated that, while "an unsaturated carboxylic compound" may be disclosed, the unsaturated carboxylic compound may comprise a mixture of unsaturated carboxylic compounds as disclosed above.

As disclosed above, the unsaturated dicarboxylic compound may be prepared by contacting at least one unsaturated carboxylic compound with at least one catalyst. In one embodiment, the catalyst may be a metathesis catalyst. The metathesis catalyst may be a homogeneous metathesis catalyst or a heterogeneous metathesis catalyst. In one embodiment, the catalyst may be a ruthenium catalyst. In another embodiment, the catalyst may be a Hoveyda-Grubbs generation 2 catalyst. As an example, the catalyst may comprise 1,3-bis-(2,4,6-trimethylphenyl)-2-(imidazolidinylidene) (dichlorophenylmethylene)(tricyclohexylphosphine)ruthenium, (1,3-Bis-(2,4,6-trimethylphenyl)-2 imidazolidinylidene)dichloro(o-isopropoxyphenylmethylene) ruthenium, or a combination of the two ruthenium catalysts. In one embodiment, the catalyst and the unsaturated carboxylic compound may be present initially at a weight ratio of about 1:1000 to about 1:10,000. Specific examples of the initial weight ratio of the catalyst to the unsaturated carboxylic compound include 1:2000, 1:4000, 1:6000, 1:8000, and ranges between any two of these values.

In addition, the catalyst may be bound to a medium when it contacts the unsaturated carboxylic compound. The medium may be a silica, a zeolite, a ceramic, a styrenic resin, or combination of those media. The bound catalyst may be formulated as small particles freely suspended in a reaction medium. Alternatively, the bound catalyst may be present in a porous block or other solid form through which the reaction mixture may flow. In another alternative, the bound catalyst may be formulated as beads placed in a column through with a reaction mixture flows. Although only a few catalyst/medium configurations have been presented above, it may be appreciated that such examples are not limiting, and that other configurations may be anticipated by this disclosure.

Systems

Figure 2:
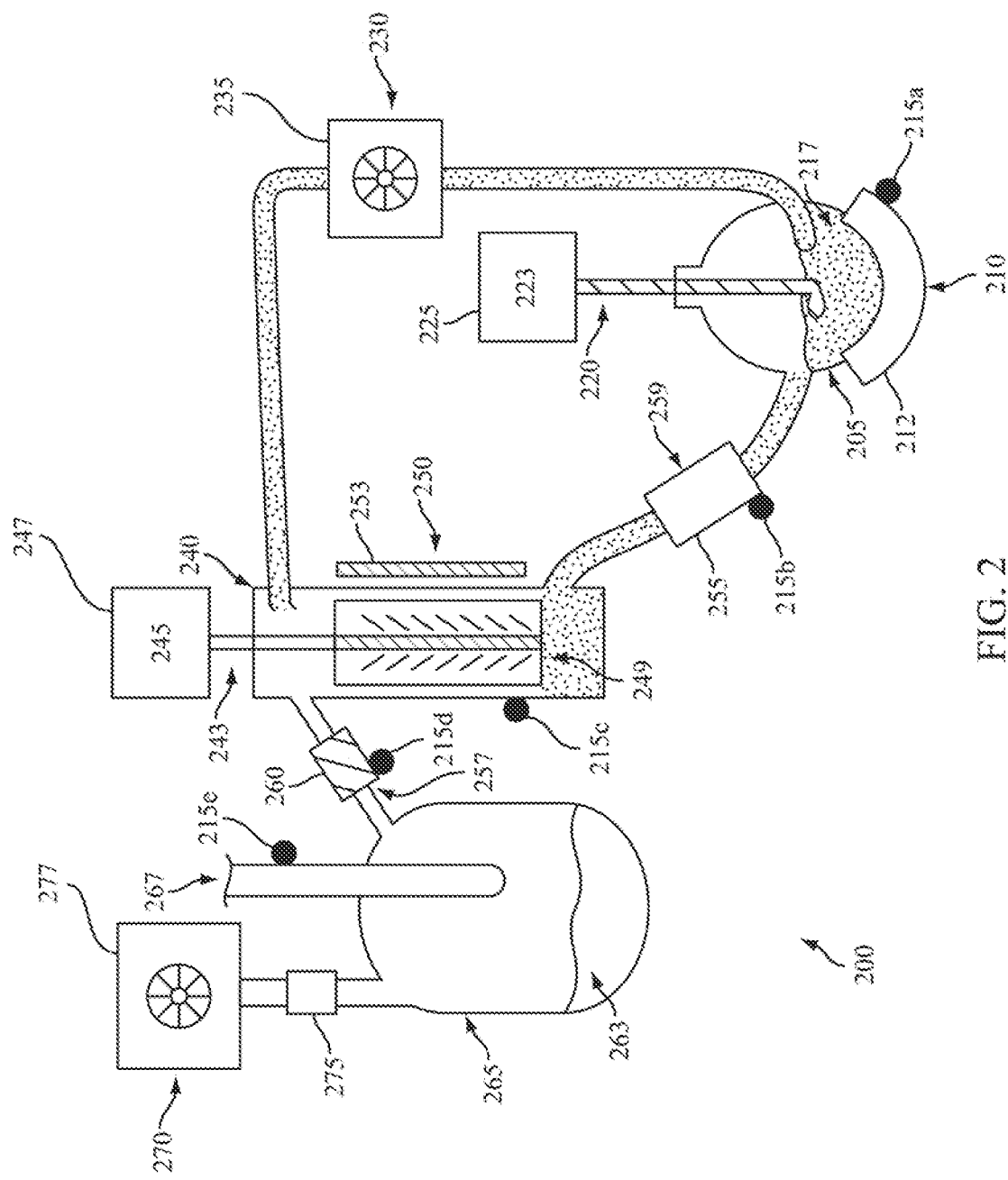
FIG. 2 illustrates an embodiment of a system for the preparation of an unsaturated dicarboxylic compound in accordance with the present disclosure.

FIG. 2 illustrates an embodiment of a system 200 that may be used to prepare the unsaturated dicarboxylic compounds. The main components include, without limitation, at least one reaction vessel 205, at least one wiped-film still 240, at least one condenser 257, at least one alkene collection vessel 265, and at least one pressure regulation system 270.

Reaction vessel 205 may contain a mixture 217 comprising an unsaturated carboxylic compound and at least one catalyst in contact with the unsaturated carboxylic compound. The mixture may be mixed in any of a variety of manners including, without limitation, a continuous stirring method. In an embodiment, the continuous stiffing method may include a stirring device 220 immersed in the mixture 217 while being controlled by a stiffing controller 223. The stiffing controller may receive control commands through a stiffing controller interface 225 to an electronic system. It may be appreciated that the stirring controller interface 225 may be used by an electronic device to control the stiffing controller 223, as well as to receive sensor data from the stirring controller. Sensor data from the stiffing controller may include, without limitation, one or more motion sensors to sense the speed and/or direction of the stirring device 220. Reaction vessel 205 may also be heated by a reaction vessel heating system 210. The reaction vessel heating system may be controlled by an electronic device through a reaction vessel heating system controller interface 212.

In one embodiment, the mixture 217 within the reaction vessel may be transported into the wiped-film still 240 by means of a mixture transport system 230. The transport system, in one embodiment, may include a pump, such as a peristaltic pump. The transport system may be controlled through a transport system control interface 235 by the electronic system. It may be appreciated that the transport system control interface 235 may be used by an electronic device to control the transport system, as well as to receive sensor data from the transport system. Types of transport system sensor data may include, without limitation, motion sensor data to determine the speed of a transport system device, fluid pressure, or fluid flow.

The wiped-film still 240 may comprise a body, at least one wiper blade 249, a wiper-blade motion system comprising, as a non-limiting example, a wiper-blade axle 243 and a wiper blade motion controller 245, and at least one wiped-film still surface heating system 250 comprising at least one heated surface. The reaction mixture 217 may be transported into the wiped-film still 240 by the transport system 230. The wiper-blade axle 243 may the cause the wiper blade(s) 249 to rotate, thereby spreading a thin film of reaction mixture onto the body of the wiped-film still 240. In one embodiment, surface heating system 250 comprising at least one heated surface may be placed in thermal contact with the body of the wiped-film still. Alternatively, the heated surface may be incorporated into the body of the still. A film of reaction mixture spread against the body of the still thus may be heated by the surface heating system 250. The heating system may be set at some temperature or range of temperatures so that the alkenes may be preferentially vaporized, leaving the reaction mixture enriched in the dicarboxylic compound. In this manner, the alkenes may be distilled from the mixture.

The wiper-blade motion system may be controlled through a wiper-blade motion system control interface 247 by the electronic system. It may be appreciated that the wiper-blade motion control interface 247 may be used by an electronic device to control the wiper-blade motion system, as well as to receive sensor data from the wiper-blade motion system. Types of wiper-blade motion system sensor data may include, without limitation, motion sensor data to determine the speed and/or direction of the wiper-blade motion. In addition, the wiped-film still heating system may be controlled through a still heating system control interface 253 by the electronic system. It may be appreciated that the still heating system control interface 253 may be used by an electronic device to control the still heating system, as well as to receive sensor data from the still heating system. Types of still heating system sensor data may include, without limitation, data related to the temperature of the heated surface.

The alkenes removed from the reaction mixture, such as through the operation of the wiped-film still, may be collected in an alkene collection vessel 265. The vaporized alkenes may be condensed on a condenser 257 to form a liquid alkene mixture 263 that may be collected in the collection vessel 265. The alkene mixture 263 may comprise any of a variety of alkenes including short-chain alkenes, long-chain alkenes, or a mixture of short-chain alkenes and long-chain alkenes. Although the term mixture is used with respect to the material collect in the alkene collection vessel, it may be understood that the mixture may in fact be composed of only one alkene species, depending on the conditions under which the reaction is run. The condenser cooling system 257 may comprise any of a variety of devices including, without limitation, a cold water circulating system, or a Peltier system. The condenser cooling system may be controlled through a condenser cooling system control interface 260 by the electronic system. It may be appreciated that the condenser cooling control interface 260 may be used by an electronic device to control the condenser cooling system, as well as to receive sensor data from the condenser cooling system. Types of condenser cooling system sensor data may include, without limitation, motion sensor data to determine the activity associated with mechanical components, such as a refrigerant circulation mechanism. In addition, the temperature of the condenser may be monitored by a temperature sensor. In addition, a second cooling system 267, such as a cold-finger, may be provided. The second cooling system may be used to remove short chain alkenes and other material not otherwise trapped by the condenser cooling system.

The temperature required for distilling the alkenes in the wiped-film still may be reduced if the pressure in the system is also reduced. Reduction of the still temperature may be useful in an example in which the reaction mixture, including the catalyst, is circulated into the wiped-film still. The catalyst may suffer degradation due to elevated temperatures, and therefore exposure of the catalyst to high temperatures at the heated surface may reduce the effectiveness of the catalyst. Consequently, if the pressure within the system—including the reaction vessel, wiped-film still, and collection vessel—is lowered, the alkenes may be removed at a lower temperature. The pressure within the system may be regulated by means of a pressure regulation system 270. The pressure regulation system may comprise any of a number of systems such as positive displacement pumps, including, without limitation, a rotary vane pump, a diaphragm pump, or a piston pump. The pressure regulation system may be controlled through a pressure regulation system control interface 277 by the electronic system. It may be appreciated that the pressure regulation control interface 277 may be used by an electronic device to control the pressure regulation system, as well as to receive sensor data from the pressure regulation system. Types of pressure regulation system sensor data may include, without limitation, motion sensor data to sense the mechanical actions associated with a positive displacement pump. The pressure regulation system may also include a pressure sensing element that may be monitored by the electronic device. Alternatively, an independent pressure sensor 275 may provide pressure data to the electronic system.

In one embodiment, the reaction mixture 217 may return to the reaction vessel 205 from the wiped-film still 240. In an embodiment, the mixture in the still may be cooled before returning to the reaction vessel by means of a return cooling system 259 placed in a return path from the still to the reaction vessel. The return path cooling system may provide a means to cool the mixture from the temperature attained at the heating surface associated with the body of the still to a temperature maintained in the reaction vessel. The mixture may be cooled according to any number of means, including, without limitation, the use of a cold water circulating system. The return cooling system may be controlled through a return cooling system control interface 255 by the electronic system. It may be appreciated that the return cooling system control interface 255 may be used by an electronic device to control the return cooling system, as well as to receive sensor data from the return cooling system. Types of return cooling system sensor data may include, without limitation, motion sensor data to sense the mechanical actions associated with the circulation of a refrigerant. Alternatively, the return cooling system sensor data may include temperature data.

It may be appreciated that the mixture may be circulated between the reaction vessel and the wiped-film still. Several variables may be monitored within the system including, but not limited to, pressure, temperature, mixture flow, and motions associated with the various mechanical components such as pumps and still components. While many of the components of the system, as disclosed above, may provide sensor data to an electronic device, separate sensors may also provide such data. For example, temperature sensors 215a-e may monitor the temperature at various stages, such as reaction mixture temperature, wiped-film still heated surface temperature, the temperature of the condenser, return flow cooling system, and secondary cooling systems. As non-limiting examples, such temperature sensors may include thermistors, thermocouples, bolometers, thermometers, resistance temperature detectors, and/or silicon band-gap temperature sensors. Additionally, the system pressure may be monitored by an independent pressure sensor 275. An electronic system receiving such data may use the data, in addition to other system parameters, to control the operations of the system, including mixing the material in the reaction vessel, the motion of the still wipers, the operation of various pumps, and cooling and heating systems.

Although FIG. 2 illustrates one embodiment of a system to prepare the unsaturated dicarboxylic compound, it may be appreciated that the other embodiments are anticipated as well. For example, the catalyst may be immobilized in a medium and the circulating reaction mixture may include only the unsaturated carboxylic compound, the unsaturated dicarboxylic compound, and the alkenes. For example, the catalyst may be associated with a medium in the form of beads that are packed in a column, through which the reaction mixture may circulate. In another embodiment, a system may allow the reaction to run in the reaction vessel for a period of time, and then the alkenes may be periodically removed under low pressure in a wiped-film still. In yet another embodiment, the wiped-film still may also include a reaction vessel, so that the reaction conditions and removal of the alkenes may occur concurrently. Further, although it has been disclosed above that the various sensors and active components of the system may transmit data to and receive control signals from a single electronic device, alternative embodiments may allow for any number of individual electronic devices to monitor and control the system. Such individual electronic devices may operate independently or in concert, and may share data and information among any or all of them.

Figure 3:
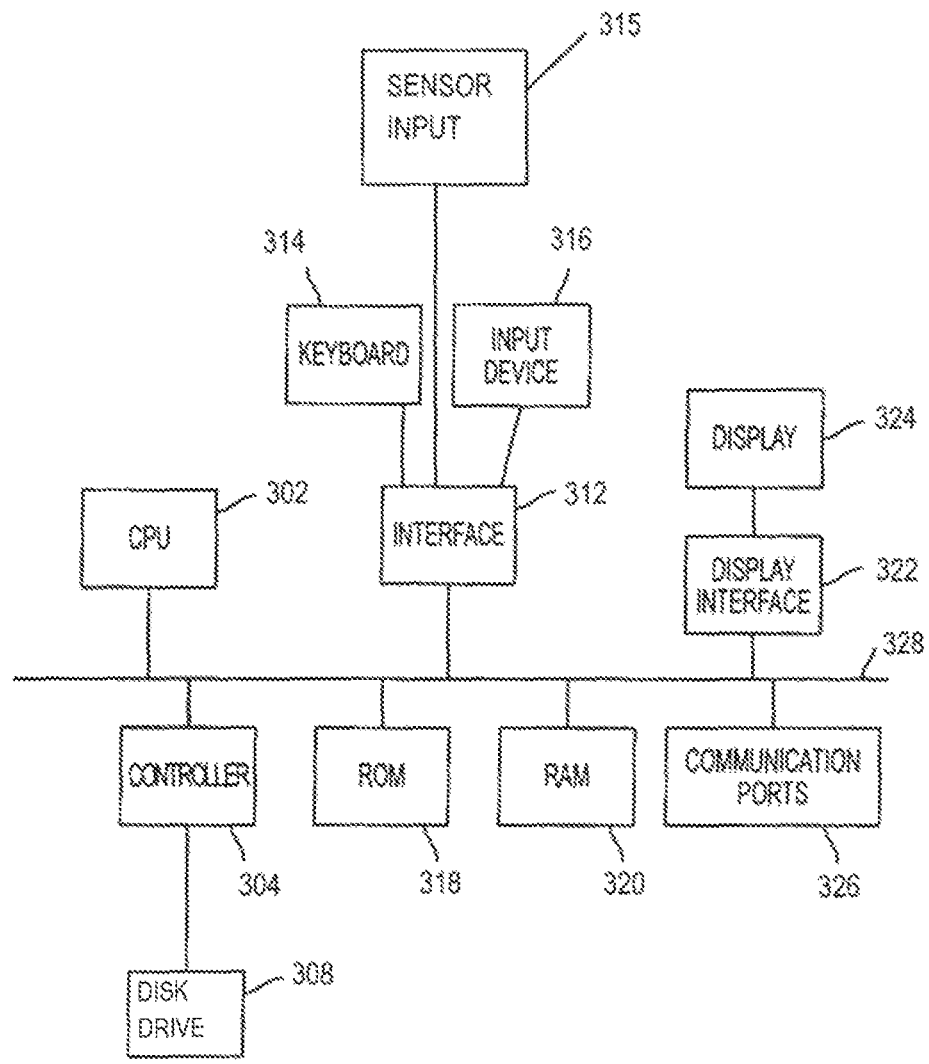
FIG. 3 illustrates an embodiment of an electronic system in accordance with the present disclosure.

FIG. 3 illustrates an embodiment of an electronic system that may be used to receive sensor data from, and transmit control data to a system for the preparation of unsaturated dicarboxylic compounds. Referring to FIG. 3, a bus 328 may serve as the main information highway interconnecting the other illustrated components of the hardware. CPU 302 is the central processing unit of the system, performing calculations and logic operations required to execute a program. Read only memory (ROM) 318 is one embodiment of a static memory device and random access memory (RAM) 320 is one embodiment of a dynamic memory device. A controller 304 may interface the system bus 328 with one or more optional disk drives 308. These disk drives may include, for example, external or internal DVD drives, CD ROM drives, or hard drives. Program instructions may be stored in the ROM 318 and/or the RAM 320. Optionally, program instructions may be stored on a computer readable medium such as a compact disk or a digital disk or other recording medium, a communications signal or a carrier wave. An optional display interface 322 may permit information from the bus 328 to be displayed on the display 324 in audio, graphic or alphanumeric format. Communication with external devices may occur using various communication ports 326. For example, communication with the reaction vessel heating system controller interface 212, the transport system control interface 235, the wiper-blade motion control interface 247, the still heating system control interface 253, the condenser cooling system interface 260, the pressure regulation system control interface 277, and the return cooling system control interface 255, may occur via one or more communication ports 326. In addition to the components disclosed above, the hardware may also include an interface 312 which allows for receipt of data from input devices such as a keyboard 314 or other input device 316 such as a mouse, remote control, pointing device and/or joystick. In addition, sensor data from any of the control systems or from other sensors such as pressure sensor 275 or temperature sensors 215a-e, may be communicated through sensor input 315 through interface 312 to bus 328.

It should be understood that any or all of the components illustrated in FIG. 3 may be part of an electronic system for monitoring and controlling the components of the system illustrated in FIG. 2. Alternative control output ports and/or sensor data input ports not otherwise specified in FIG. 3 may also be part of such an electronic system. Further, more than one electronic system may be used for system monitoring and control. If more than one electronic system is used for data acquisition and control, the electronic systems may act independently or in concert, and may have one or more means of communicating information between and among them, including without limitation, internet communications or wireless communications.

It is understood that the embodiment illustrated in FIG. 2 is non-limiting, and components illustrated as separate may be combined in appropriate ways. For example, any one or more of stirring device 220, heating system 210, and temperature sensor 215a may be incorporated into reaction vessel 205. As another example, any one or more of mixture transport system 230, condenser 257, and pressure regulation system 270 may be incorporated into wiped-film still 240. Alternative combinations of components are also anticipated by this disclosure.

Methods

Figure 4:
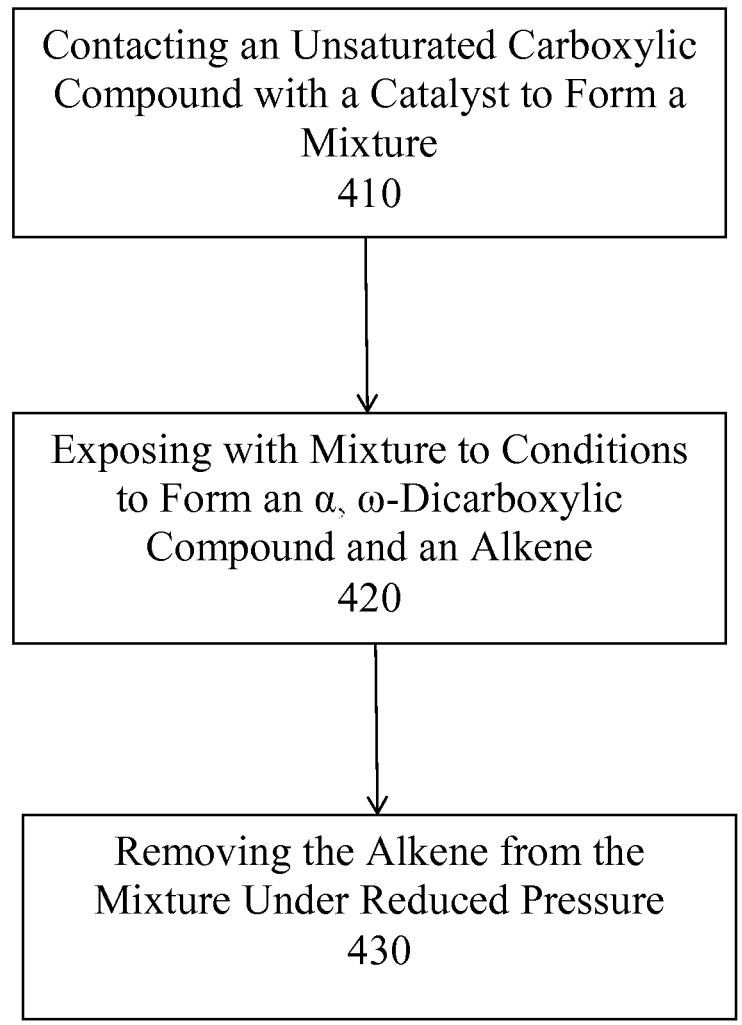
FIG. 4 is a flow chart of an embodiment of a method in accordance with the present disclosure.

FIG. 4 is a flow chart illustrating an embodiment of a method of preparing an unsaturated α,ω-dicarboxylic compound from an unsaturated carboxylic compound in the present of at least one catalyst.

In one embodiment, an unsaturated carboxylic compound may contact at least one catalyst to form a mixture 410. In another embodiment, a mono-unsaturated carboxylic compound may contact at least one metathesis catalyst to form a mixture. In another embodiment, contacting includes mixing. In yet another embodiment, contacting includes stirring continuously.

The unsaturated carboxylic compound may comprise at least a carboxyl end. Further, the carboxyl end may be attached to a trailing component. The carboxyl end may further be conjugated to a leaving group. The leaving group may include an —O—$R_1$, an —S—$R_2$, an —NH—$R_3$, or an —N($R_4$)($R_5$) group. It is therefore understood that an unsaturated carboxylic compound may comprise at least a carboxyl end, in which the carboxyl end may be conjugated to a leaving group thereby forming at least an ester, a thioester, a primary amide, or a secondary amide bond.

Groups $R_1$-$R_5$ may comprise any of a number of organic substituents, including, but not limited to, aliphatic groups and aromatic groups. In one embodiment, the leaving group may include an O-aliphatic group, an O-aromatic group, an S-aliphatic group, an S-aromatic group, an N-primary amine group, or an N-secondary amine group. In one embodiment, the unsaturated carboxylic compound may be an unsaturated carboxylic acid compound. In another embodiment, the unsaturated carboxylic compound may be an unsaturated carboxylic acid ester compound. In yet another embodiment, the unsaturated carboxylic compound may be an unsaturated carboxylic acid methyl ester compound. In another embodiment, the leaving group may include a hydroxyl group, a methoxy group, an ethoxy group, a butoxy group, an isobutoxy group, a propoxy group, an isopropoxy group, a phenoxy group, a methyl sulfide group, an ethyl sulfide group, a butyl sulfide group, an isobutyl sulfide group, a propyl sulfide group, an isobutyl sulfide group, a phenyl sulfide group, a methyl amine group, an ethyl amine group, a butyl amine group, an isobutyl amine group, a propyl amine group, an isopropyl amine group, an N,N-dimethyl amine group, an N,N-di-ethyl amine group, an N,N-dibutyl amine group, an N,N-di-isobutyl amine group, an N,N-dipropyl amine group, or an N,N-di-isopropyl amine group.

The trailing component of an unsaturated carboxylic compound may include a variety of organic groups including linear chain and branched chain groups. In one embodiment, the trailing group may include a mono-unsaturated chain or a poly-unsaturated chain. In some embodiments, the liner chain may comprise "n" carbon atoms, where "n" may be an integer from about 5 to about 30. In some embodiments, "n" may be an integer from about 16 to about 22. In still another embodiment, "n" may be about 18. The integer can be an even number or an odd number. Examples of even number include 6, 8, 10, 12, 14, 16, 18, 20, 22, 24, 26, 28, 30, and ranges between any two of these values. Examples of odd numbers include 5, 7, 9, 11, 13, 15, 17, 19, 21, 23, 25, 27, 29, and ranges between any two of these values.

One embodiment of a poly-unsaturated linear chain trailing component of an unsaturated carboxylic compound may include a propenyl repeat section within the linear chain. The propenyl moiety may be repeated "x" times within the repeat section, where "x" may be an integer from 0 to 4. In some embodiments, "x" may be 0, 1, 2, 3, or 4.

The trailing component may also include lengths of straight chain alkane moieties attached at either one or both ends of the propenyl repeat section. In one embodiment, an alkane moiety may have about 1 to about 14 carbons. In another embodiment, an alkane moiety may have about 7 to about 11 carbons. In still another embodiment, an alkane moiety may have about 9 carbons. Specific examples of the number of carbons include, 1, 2, 3, 4, 5, 6, 7, 8, 9, 10, 11, 12, 13, 14, and ranges between any two of these values. It is understood that an alkane moiety attached at a first end of the propenyl repeat section may have the same number of carbons as an alkane moiety attached at the second end of the propenyl repeat section. Alternatively, the alkane moiety attached at a first end of the propenyl repeat section may have a different number of carbons than the alkane moiety attached at the second end of the propenyl repeat section.

Another embodiment of a trailing component may include any number or distribution of unsaturated carbon-carbon bonds along a linear chain. The trailing component may further include one or more functional groups including, without limitation, an epoxy group, an alcohol group, or a pendant vinyl group. The trailing component of a carboxylic compound may include any or all of these groups, or other functional groups.

It may be appreciated that the stereo-isomeric configuration about any one of the carbon-carbon double bonds of an unsaturated carboxylic compound may have a cis configuration or a trans configuration (or alternatively stated, E- or Z-configuration). A poly-unsaturated carboxylic compound may include cis isomers at all carbon-carbon double bonds, trans isomers at all carbon-carbon double bonds, or a combination of cis isomers at some carbon-carbon double bonds and trans isomers at the other carbon-carbon double bonds. It may further be appreciated that the unsaturated $\alpha,\omega$-dicarboxylic compound resulting from the unsaturated carboxylic compound, may similarly have any number of stereo-isomeric configurations about their carbon-carbon double bonds. An unsaturated dicarboxylic compound may have all cis configurations, all trans configurations, or a mixture of cis configurations and trans configurations about the double bonds.

It may be appreciated that, while "an unsaturated carboxylic compound" may be disclosed, the unsaturated carboxylic compound may comprise a mixture of unsaturated carboxylic compounds as disclosed above.

The unsaturated carboxylic compound may be contacted with a catalyst. In one embodiment, the catalyst may be a metathesis catalyst. The metathesis catalyst may be a homogeneous metathesis catalyst or a heterogeneous metathesis catalyst. In one embodiment, the catalyst may be a ruthenium catalyst. In another embodiment, the catalyst may be a Hoveyda-Grubbs generation 2 catalyst. As an example, the catalyst may comprise 1,3-bis-(2,4,6-trimethylphenyl)-2-(imidazolidinylidene)(dichlorophenylmethylene)(tricyclohexylphosphine)ruthenium, (1,3-Bis-(2,4,6-trimethylphenyl)-2 imidazolidinylidene)dichloro(o-isopropoxyphenylmethylene)ruthenium, or a combination of the two ruthenium catalysts. In one embodiment, the catalyst and the unsaturated carboxylic compound may be present initially at a weight ratio of about 1:1000 to about 1:10,000. Specific examples of the initial weight ratio of the catalyst to the unsaturated carboxylic compound include 1:2000, 1:4000, 1:6000, 1:8000, and ranges between any two of these values.

In addition, the catalyst may be bound to a medium when it contacts the unsaturated carboxylic compound. The medium may be a silica, a zeolite, a ceramic, a styrenic resin, or combination of those media. The bound catalyst may be formulated as small particles freely suspended in a reaction medium. Alternatively, the bound catalyst may be present in a porous block or other solid form through which the reaction mixture may flow. In another alternative, the bound catalyst may be formulated as beads placed in a column through with a reaction mixture flows. Although only a few catalyst/medium configurations have been presented above, it may be appreciated that such examples are not limiting, and that other configurations may be anticipated by this disclosure.

In one embodiment, the mixture comprising the unsaturated carboxylic compound and catalyst may be exposed to conditions favorable to the formation of an unsaturated $\alpha,\omega$-dicarboxylic compound and an alkene compound 420. In another embodiment, the mixture comprising a mono-unsaturated carboxylic compound and a metathesis catalyst may be subjected to conditions favorable to the formation of a mono-unsaturated $\alpha,\omega$-dicarboxylic compound and an alkene compound.

An unsaturated $\alpha,\omega$-dicarboxylic compound may comprise at least a pair of carboxyl ends. Further, the carboxyl ends may be joined by an intermediate component. Each carboxyl end may further be conjugated to a leaving group. The leaving groups may independently include an —O—$R_1$, an —S—$R_2$, an —NH—$R_3$, or an —N($R_4$)($R_5$) group. Both leaving groups may be the same type of group. Alternatively, although the two leaving groups may be different types of groups. It is therefore understood that an unsaturated $\alpha,\omega$- dicarboxylic compound may comprise at least a pair of carboxyl ends, in which each carboxyl end may be conjugated to a leaving group thereby forming at least one or more of an ester, a thioester, a primary amide, or a secondary amide bond.

Groups $R_1$-$R_5$ may comprise any of a number of organic substituents, including, but not limited to, aliphatic groups and aromatic groups. In one embodiment, either one or both of the leaving groups may include an O-aliphatic group, an O-aromatic group, an S-aliphatic group, an S-aromatic group, an N-primary amine group, or an N-secondary amine group. In one embodiment, the unsaturated $\alpha,\omega$-dicarboxylic compound may be a dicarboxylic acid monomer. In one embodiment, the unsaturated $\alpha,\omega$-dicarboxylic compound may be an unsaturated $\alpha,\omega$-dicarboxylic acid compound. In another embodiment, the unsaturated $\alpha,\omega$-dicarboxylic compound may be an $\alpha,\omega$-dicarboxylic acid ester compound. In yet another embodiment, the unsaturated $\alpha,\omega$-dicarboxylic compound may be an unsaturated $\alpha,\omega$-dicarboxylic acid methyl ester compound. In still another embodiment, the unsaturated $\alpha,\omega$-dicarboxylic compound may be an unsaturated $\alpha,\omega$-dicarboxylic acid methyl ester compound. In another embodiment, either one or both of the leaving groups may include a hydroxyl group, a methoxy group, an ethoxy group, a butoxy group, an isobutoxy group, a propoxy group, an isopropoxy group, a phenoxy group, a methyl sulfide group, an ethyl sulfide group, a butyl sulfide group, an isobutyl sulfide group, a propyl sulfide group, an isobutyl sulfide group, a phenyl sulfide group, a methyl amine group, an ethyl amine group, a butyl amine group, an isobutyl amine group, a propyl amine group, an isopropyl amine group, an N,N-dimethyl amine group, an N,N-di-ethyl amine group, an N,N-dibutyl amine group, an N,N-di-isobutyl amine group, an N,N-dipropyl amine group, or an N,N-di-isopropyl amine group.

The intermediate component of an unsaturated $\alpha,\omega$-dicarboxylic compound may include a variety of organic groups including linear chain and branched chain groups. In one embodiment, the intermediate component may include an unsaturated linear chain. In another embodiment, the intermediate component may include a mono-unsaturated chain or a poly-unsaturated chain. In some embodiments, the linear chain may comprise "n" carbon atoms, where "n" may be an integer from about 5 to about 30. In some embodiments, "n" may be an integer from about 16 to about 22. In still another embodiment, "n" may be about 18. The integer can be an even number or an odd number. Examples of even number include 6, 8, 10, 12, 14, 16, 18, 20, 22, 24, 26, 28, 30, and ranges between any two of these values. Examples of odd numbers include 5, 7, 9, 11, 13, 15, 17, 19, 21, 23, 25, 27, 29, and ranges between any two of these values.

In one embodiment, a poly-unsaturated linear chain intermediate component of an unsaturated $\alpha,\omega$-dicarboxylic compound may include a propenyl repeat section within the linear chain. The propenyl moiety may be repeated "x" times within the repeat section, where "x" may be an integer from 0 to 4. In some embodiments, "x" may be 0, 1, 2, 3, or 4.

The intermediate component may also include lengths of straight chain alkane moieties attached at either one or both ends of the propenyl repeat section. In one embodiment, an alkane moiety may have about 1 to about 14 carbons. In another embodiment, an alkane moiety may have about 7 to about 11 carbons. In still another embodiment, an alkane moiety may have about 9 carbons. Specific examples of the number of carbons include, 1, 2, 3, 4, 5, 6, 7, 8, 9, 10, 11, 12, 13, 14, and ranges between any two of these values. It is understood that an alkane moiety attached at a first end of the propenyl repeat section may have the same number of carbons as an alkane moiety attached at the second end of the propenyl repeat section. Alternatively, the alkane moiety attached at a first end of the propenyl repeat section may have a different number of carbons than the alkane moiety attached at the second end of the propenyl repeat section.

In another embodiment, the intermediate component may include any number or distribution of unsaturated carbon-carbon bonds along a linear chain. The intermediate component may further include one or more functional groups including, without limitation, an epoxy group, an alcohol group, or a pendant vinyl group. The intermediate component of an unsaturated $\alpha,\omega$-dicarboxylic compound may include any or all of these groups, or other functional groups.

It may be appreciated that the stereo-isomeric configuration about any one of the carbon-carbon double bonds of an unsaturated $\alpha,\omega$-dicarboxylic compound may have a cis configuration or a trans configuration (or alternatively stated, E- or Z-configuration). A poly-unsaturated $\alpha,\omega$-dicarboxylic compound may include cis isomers at all carbon-carbon double bonds, trans isomers at all carbon-carbon double bonds, or a combination of cis isomers at some carbon-carbon double bonds and trans isomers at the other carbon-carbon double bonds.

It may be appreciated that, while "an unsaturated $\alpha,\omega$-dicarboxylic compound" may be disclosed, the unsaturated $\alpha,\omega$-dicarboxylic compound may comprise a mixture of unsaturated $\alpha,\omega$-dicarboxylic compounds as disclosed above.

The alkene compound may include a short-chain alkene, a long-chain alkene, or a mixture of short-chain and long-chain alkene compounds.

In one embodiment, an alkene compound may include a propenyl repeat section within a linear chain. The propenyl moiety may be repeated "x" times within the repeat section, where "x" may be an integer from 0 to 4. In some embodiments, "x" may be 0, 1, 2, 3, or 4.

The alkene compound may also include lengths of straight chain alkane moieties attached at either one or both ends of the propenyl repeat section. In one embodiment, an alkane moiety may have about 1 to about 14 carbons. In another embodiment, an alkane moiety may have about 7 to about 11 carbons. In still another embodiment, an alkane moiety may have about 9 carbons. Specific examples of the number of carbons include, 1, 2, 3, 4, 5, 6, 7, 8, 9, 10, 11, 12, 13, 14, and ranges between any two of these values. It is understood that an alkane moiety attached at a first end of the propenyl repeat section may have the same number of carbons as an alkane moiety attached at the second end of the propenyl repeat section. Alternatively, the alkane moiety attached at a first end of the propenyl repeat section may have a different number of carbons than the alkane moiety attached at the second end of the propenyl repeat section.

In another embodiment, the alkene compound may include at least one unsaturated carbon-carbon bond along a linear chain. The alkene compound may further include one or more functional groups including, without limitation, an epoxy group, an alcohol group, or a pendant vinyl group. The alkene compound may include any or all of these groups, or other functional groups.

It may be appreciated that the stereo-isomeric configuration about any one of the carbon-carbon double bonds of an alkene compound may have a cis configuration or a trans configuration (or alternatively stated, E- or Z-configuration). A poly-unsaturated alkene compound may include cis isomers at all carbon-carbon double bonds, trans isomers at all carbon-carbon double bonds, or a combination of cis isomers at some carbon-carbon double bonds and trans isomers at the other carbon-carbon double bonds.

Examples of alkene compounds may include any one or more of 3-hexene, 4-heptene, 4-octene, non-3,6-diene, 6-dodecene, 6-pentadecene, octadec-6,9-diene, or 9-octadecene.

Under suitable conditions, an unsaturated α,ω-dicarboxylic compound and an alkene compound may be formed 420. In one embodiment, suitable conditions may include heating the mixture to a temperature of about 30° C. to about 100° C. In one embodiment, suitable conditions may include heating the mixture to a temperature of about 40° C. to about 90° C. In another embodiment, suitable conditions may include heating the mixture to a temperature of about 75° C. Specific examples of temperatures include about 30° C., about 40° C., about 50° C., about 60° C., about 70° C., about 80° C., about 90° C., and ranges between any two of these values. In an embodiment, the mixture may be heated for about 1 hour to about 10 hours. In an embodiment, the mixture may be heated for about 2 hours to about 8 hours. In yet another embodiment, the mixture may be heated for about 5 hours. Specific examples of time include about 2 hours, about 3 hours, about 4 hours, about 5 hours, about 6 hours, about 7 hours, about 8 hours, about 9 hours, about 10 hours, and ranges between any two of these values.

The alkene compound or compounds formed during the reaction may further be removed under reduced pressure from the mixture 430. In one embodiment, the reduced pressure may be from about 50 mTorr (6.7 Pa) to about 1000 mTorr (133 Pa). In one embodiment, the reduced pressure may be from about 100 mTorr (13.3 Pa) to about 400 mTorr (53.3 Pa). In yet another embodiment, the reduced pressure may be about 240 mTorr (32 Pa). Specific examples of pressure include about 50 mTorr (6.7 Pa), about 150 mTorr (20.0 Pa), about 250 mTorr (33.3 Pa), about 350 mTorr (46.7 Pa), about 450 mTorr (60.0 Pa), about 550 mTorr (73.3 Pa), about 650 mTorr (86.7 Pa), about 750 mTorr (100.0 Pa), about 850 mTorr (113.3 Pa), about 950 mTorr (126.7 Pa), and ranges between any two of these values. As the method includes removing part of the reaction products (the alkene compound) from the reaction mixture, the formation of the unsaturated α,ω-dicarboxylic compound in the reaction process may be favored. In one embodiment, an amount of the unsaturated carboxylic compound may be converted to an amount of the unsaturated α,ω-dicarboxylic compound with at least a 50% yield. In one embodiment, an amount of the unsaturated carboxylic compound may be converted to an amount of the unsaturated α,ω-dicarboxylic compound with at least a 65% yield. In still another embodiment, an amount of the unsaturated carboxylic compound may be converted to an amount of the unsaturated α,ω-dicarboxylic compound with at least an 80% yield. Specific examples of yield include about 50%, about 60%, about 70%, about 80%, about 90%, and ideally about 100%. While the exposing step 420 and removing step 430 are illustrated in FIG. 4 as being distinct, it is understood that the two steps may occur concurrently.

The removing step 430 may be accomplished according to a number of means. In one embodiment, removing the alkenes may be accomplished by distilling the alkene compound from the mixture. In addition, the distilled alkene compound may be condensed using a condenser to form a liquid alkene compound which may be collected from the condenser in a collection vessel. In another embodiment, the alkenes may be distilled using a wiped-film still. The wiped-film still may include at least one wiper blade that is moved by means of a wiper-blade axle. The mixture in the wiped-film still may be deposited as a thin film by the wiper blade on a surface of the wiped-film still. The surface may be a heated surface or may be in thermal contact with a heated surface to raise the temperature of the film. In one embodiment, the surface may be heated to a temperature of about 40° C. to about 160° C. In one embodiment, the surface may be heated to a temperature of about 70° C. to about 140° C. In yet another embodiment, the surface may be heated to a temperature of about 110° C. Specific examples of surface temperature include about 40° C., about 60° C., about 80° C., about 100° C., about 120° C., about 140° C., about 160° C., and ranges between any two of these values.

It may be appreciated that the preparation of an unsaturated α,ω-dicarboxylic compound according to the methods disclosed above, may readily lend itself to automation. For example, the reaction mixture may be circulated through a reaction vessel and a still, such as a wiped-film still. Conditions in the reaction vessel, the thin-film still, or both devices may be monitored. Similarly, operations in the reaction vessel, the thin-film still, or both devices may be controlled.

For example, the temperature of the mixture in the reaction vessel and/or in the wiped-film still may be monitored by one or more temperature sensors. Heating systems, such as a reaction vessel heating system and a wiped-film still surface heating system, may be controlled to maintain an appropriate temperature. The reduced pressure in the wiped-film still and/or the reaction vessel may be monitored by one or more pressure sensors. The pressure may then be controlled by means of a pressure regulation system such as by a vacuum pump. The activities of various mechanical systems, such as a mixing system in the reaction vessel or a wiped-film still wiper-blade motion system in the thin-film still, may be monitored by a variety of sensors associated with the motion of the mechanical parts. The mechanical systems may then be controlled to move according to required system parameters.

In one embodiment, the mixture may be circulated by a mixture transport system, such as a pump, in which the pump activity may be monitored and controlled, such as the pump speed. A flow sensor, measuring the rate of flow of the mixture from the reaction vessel to the still may also provide data for pump activity control. In another embodiment, a condenser cooling system used to condense the alkene compound may be monitored and controlled. The condenser may be monitored for temperature. In one embodiment, the condenser may use circulating chilled water or other fluid to condense the alkene compound. The flow rate and/or the temperature of the cooling fluid may be controlled in order to control the temperature of the condenser. In one embodiment, the reaction mixture returning from the wiped-film still to the reaction vessel may also be cooled along the return path by another cooling system to preserve the activity of the catalyst. The temperature of the return path cooling system may also be monitored and controlled in a manner similar to that of the condenser.

It is understood that the data available from any or all of the sensors disclosed above may be transmitted to one or more electronic systems configured to monitor and/or store the data. The data may also be used at least in part by one or more electronic systems to control the various operations of the system as disclosed above, including but not limited to the operation of heaters, coolers, condensers, pumps, and moving mechanical systems. It is further understood that a single electronic device may be used for such monitoring and control, or a number of electronic devices may be used working either separately or in concert.

In addition, the activity of the one or more electronic devices may be programmed into the electronic systems to control the preparation system in a fixed manner. Alternatively, a user of the one or more electronic systems may be able to control the electronic systems by specifying parameters associated with one or more of the temperatures, pressures, fluid flow, and mechanical operation of the preparation system as disclosed above. The user may be presented with an interface to simplify system programming, the interface including, as non-limiting examples, graphical displays, drop-down menus, and/or text-entry displays. The user may use a keypad, mouse, or a touch-screen interface in order to effect such programming.

EXAMPLES

Example 1

Preparation of a Mono-unsaturated α,ω-dicarboxylic Compound with Alkene Removal

In a reaction flask, about 500 g of a mixture of high oleic acid fatty acid methyl esters (an unsaturated carboxylic compound) was combined with about 250 mg of (1,3-Bis-(2,4,6-trimethylphenyl)-2-imidazolidinylidene)dichloro(o-isopropoxyphenylmethylene)ruthenium (a metathesis catalyst). The reaction flask was connected to a magnetically-coupled pump to permit circulation of the reaction mixture to a 2" (about 5 cm.) wiped-film still. The mixture from the still was returned to the reaction flask. The still was heated to about 110° C., and the preparation system, including the reaction flask, still, and alkene condenser, was subjected to a reduced pressure of about 240 mTorr (32 Pa). High molecular weight alkenes, having about 8 or more total carbon atoms, were collected by a condenser coupled to the still, while the low molecular weight alkenes were condensed on a liquid nitrogen trap. The reaction conditions were run for about 5 hours. After the reaction was completed, the reaction mixture was assayed for components and found to contain about 84% mono-unsaturated α,ω-dicarboxylic di-ester, 0.65% high molecular weight alkenes, having about 14 or more carbon atoms, and about 15% unreacted fatty acid methyl ester.

Example 2

Preparation of a Mono-unsaturated α,ω-dicarboxylic Compound without Alkene Removal About 15 mg of a metathesis catalyst comprising dichloro [1,3-bis(2,4,6-trimethylphenyl)-2-imidazolidinylidene] (benzylidene)bis(3-bromopyridine)ruthenium(II) immobilized on a siliceous support (a metathesis catalyst), and 2.37 ml toluene were combined in a reaction vessel and heated at about 60° C. To this first mixture about 0.131 ml of oleic acid methyl ester (an unsaturated carboxylic compound) was added to form a second mixture. The second mixture was heated at about 60° C. under an Ar atmosphere for about 2 hours with constant stirring. Under these conditions, the percent yield of the resulting mono-unsaturated dimethyl ester compared to the initial amount of oleic acid methyl ester was about 55%.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity.

It will be understood by those within the art that, in general, terms used in this disclosure, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A method of preparing an unsaturated $\alpha,\omega$-dicarboxylic compound, the method comprising:
   contacting, in a first reaction vessel, at least one unsaturated carboxylic compound and at least one catalyst to form a mixture;
   exposing, in the first reaction vessel, the mixture to conditions suitable to form at least one unsaturated $\alpha,\omega$-dicarboxylic compound and at least one alkene compound;
   circulating at least a portion of the mixture between the first reaction vessel and a second vessel; and
   removing the alkene compound from the mixture under a reduced pressure in the second vessel.

2. The method of claim 1, wherein contacting at least one unsaturated carboxylic compound comprises contacting at least one unsaturated carboxylic compound having a linear chain of "n" carbon atoms, where "n" is an integer of about 5 to about 30.

3. The method of claim 1, wherein contacting at least one unsaturated carboxylic compound comprises contacting at least one unsaturated carboxylic compound having a first leaving group conjugated at a carboxyl group terminus.

4. The method of claim 1, wherein contacting at least one unsaturated carboxylic compound and at least one catalyst comprises contacting at least one unsaturated carboxylic compound and at least one metathesis catalyst.

5. The method of claim 1, wherein contacting at least one unsaturated carboxylic compound and at least one catalyst comprises contacting at least one unsaturated carboxylic compound and at least one catalyst at a weight ratio of an amount of the at least one catalyst to an amount of the unsaturated carboxylic compound of about 1:1000 to about 1:10,000.

6. The method of claim 1, wherein contacting at least one unsaturated carboxylic compound and at least one catalyst comprises contacting at least one unsaturated carboxylic compound and at least one catalyst bound to a medium.

7. The method of claim 1, wherein exposing the mixture to conditions suitable to form at least one unsaturated $\alpha,\omega$-dicarboxylic compound and at least one alkene compound comprises heating the mixture to a first temperature of about 30° C. to about 100° C.

8. The method of claim 1, wherein exposing the mixture to conditions suitable to form at least one unsaturated $\alpha,\omega$-dicarboxylic compound and at least one alkene compound comprises heating the mixture for about 1 hour to about 10 hours.

9. The method of claim 1, wherein removing the alkene compound from the mixture under a reduced pressure comprises removing the alkene compound from the mixture under a pressure of about 50 mTorr (6.7 Pa) to about 1000 mTorr (133 Pa).

10. The method of claim 1, wherein exposing the mixture to conditions suitable to form at least one unsaturated $\alpha,\omega$-dicarboxylic compound and at least one alkene compound comprises exposing the mixture to conditions suitable to convert an amount of the unsaturated carboxylic compound to an amount of the unsaturated $\alpha,\omega$-dicarboxylic compound with at least a 50% yield.

11. The method of claim 1, wherein removing the alkene compound from the mixture comprises:
    distilling the alkene compound from the mixture;
    condensing the alkene compound on a condenser; and
    collecting the alkene compound from the condenser.

12. The method of claim 11, wherein distilling the alkene compound from the mixture comprises distilling the alkene compound using a wiped-film still.

13. The method of claim 1, further comprising:
    monitoring at least one operation of the first reaction vessel, the second vessel, or the first reaction vessel and the second vessel; and
    controlling the operation of the first reaction vessel, the second vessel, or the first reaction vessel and the second vessel.

14. The method of claim 1, further comprising monitoring the conditions via at least one sensor comprising one or more of a temperature sensor, a pressure sensor, a motion sensor, and a flow sensor.

15. The method of claim 1, further comprising controlling the conditions by transmitting at least one control signal from an electronic system to one or more of a pressure regulation system, a mixture transport system, a first reaction vessel heating system, a second vessel surface heating system, a second vessel wiper-blade motion system, a condenser cooling system, and a cooling system of a return path from the second vessel to the first reaction vessel.

16. A method of preparing a mono-unsaturated $\alpha,\omega$-dicarboxylic compound, the method comprising:
    contacting, in a first reaction vessel, a mono-unsaturated carboxylic compound and at least one metathesis catalyst to form a mixture;
    exposing, in the first reaction vessel, the mixture to conditions suitable to form a mono-unsaturated $\alpha,\omega$-dicarboxylic compound and an alkene compound;
    circulating at least a portion of the mixture between the first reaction vessel and a second vessel comprising a wiped film-still; and
    removing, under a reduced pressure, the alkene compound from the portion of the mixture in the second vessel.

17. The method of claim 16, wherein contacting a mono-unsaturated carboxylic compound comprises contacting a mono-unsaturated carboxylic compound having a linear chain of "n" carbon atoms, where "n" is an integer of about 5 to about 30.

18. The method of claim 16, wherein contacting a mono-unsaturated carboxylic compound comprises contacting a mono-unsaturated carboxylic compound having a first leaving group conjugated at a carboxyl group terminus.

19. The method of claim 16, wherein contacting a mono-unsaturated carboxylic compound and at least one metathesis catalyst comprises contacting a mono-unsaturated carboxylic compound and at least one metathesis catalyst at a weight ratio of an amount of the metathesis catalyst to an amount of the mono-unsaturated carboxylic compound of about 1:1000 to about 1:10,000.

20. The method of claim 16, wherein contacting a mono-unsaturated carboxylic compound and at least one metathesis catalyst comprises contacting a mono-unsaturated carboxylic compound and at least one metathesis catalyst bound to a medium.

21. The method of claim 16, wherein exposing the mixture to conditions suitable to form a mono-unsaturated α,ω-dicarboxylic compound and an alkene compound comprises heating the mixture to a first temperature of about 30° C. to about 100° C.

22. The method of claim 16, wherein exposing the mixture to conditions suitable to form a mono-unsaturated α,ω-dicarboxylic compound and an alkene compound comprises heating the mixture for about 1 hour to about 10 hours.

23. The method of claim 16, wherein removing, under a reduced pressure, the alkene compound comprises removing under a pressure of about 50 mTorr (6.7 Pa) to about 1000 mTorr (133 Pa) the alkene compound.

24. The method of claim 16, wherein exposing the mixture to conditions suitable to form a mono-unsaturated α,ω-dicarboxylic compound and an alkene compound comprises exposing the mixture to conditions suitable to convert an amount of the mono-unsaturated carboxylic compound to an amount of the mono-unsaturated α,ω-dicarboxylic compound with at least a 50% yield.

25. The method of claim 16, further comprising:
monitoring at least one operation of the first reaction vessel, the second vessel, or the first reaction vessel and the second vessel; and
controlling the operation of the first reaction vessel, the second vessel, or the first reaction vessel and the second vessel.

26. A system for preparing an unsaturated α,ω-dicarboxylic compound, the system comprising:
a reaction vessel configured to receive at least one unsaturated carboxylic compound, the reaction vessel comprising:
a catalyst bound to a medium, and
a reaction vessel heating system;
a second vessel in fluid communication with the reaction vessel, the second vessel comprising:
a distillation system, and
a pressure regulation system;
a fluid transport system configured to circulate a fluid between the reaction vessel and the second vessel; and
an electronic system configured to control one or more of the reaction vessel heating system, the pressure regulation system, and the fluid transport system.

27. The system of claim 26, wherein the catalyst bound to a medium comprises a Hoveyda-Grubbs generation 2 catalyst bound to a solid medium.

28. The system of claim 27, wherein the solid medium comprises a silica, a zeolite, a ceramic, a styrenic resin, or any combination thereof.

29. The system of claim 26, wherein the catalyst bound to a medium is formulated as a plurality of beads.

30. The system of claim 26, wherein the distillation system comprises a wiped-film still.

31. A method of preparing an unsaturated α,ω-dicarboxylic compound, the method comprising:
contacting, in a first reaction vessel, a first mixture of high oleic acid fatty acid methyl esters and at least one metathesis catalyst to form a second mixture;
exposing, in the first reaction vessel, the second mixture to conditions suitable to form at least one unsaturated α,ω-dicarboxylic compound and at least one alkene compound;
pumping at least a portion of the second mixture from the first reaction vessel to a second vessel comprising a wiped-film still;
heating the wiped-film still to a temperature of about 110° C. and reducing the pressure of the wiped-film still to a pressure of about 32 Pa;
condensing the at least one alkene compound on a condenser in fluid communication with the second vessel; and
returning the at least portion of the second mixture from the second vessel to the first reaction vessel.

32. The method of claim 31, wherein the metasthesis catalyst is a Hoveyda-Grubbs generation 2 catalyst.

33. The method of claim 31, wherein exposing the second mixture to conditions suitable to form at least one unsaturated α,ω-dicarboxylic compound and at least one alkene compound comprises exposing the second mixture for about 5 hours to conditions suitable to form at least one unsaturated α,ω-dicarboxylic compound and at least one alkene compound.

* * * * *

UNITED STATES PATENT AND TRADEMARK OFFICE
CERTIFICATE OF CORRECTION

PATENT NO. : 9,126,922 B2  
APPLICATION NO. : 13/430090  
DATED : September 8, 2015  
INVENTOR(S) : Allan Page 1 of 1

It is certified that error appears in the above-identified patent and that said Letters Patent is hereby corrected as shown below:

In the Specification

In Column 4, Line 56, delete "stiffing method" and insert -- stirring method --, therefor.

In Column 4, Line 58, delete "stiffing controller 223. The stiffing controller" and insert -- stirring controller 223. The stirring controller --, therefor.

In Column 4, Line 59, delete "stiffing controller" and insert -- stirring controller --, therefor.

In Column 4, Line 62, delete "stiffing controller" and insert -- stirring controller --, therefor.

In Column 4, Line 64, delete "stiffing controller" and insert -- stirring controller --, therefor.

In Column 15, Line 55, delete "stiffing." and insert -- stirring. --, therefor.

In Column 16, Line 51, delete ""recitations,"" and insert -- "two recitations, --, therefor.

Signed and Sealed this  
Twenty-eighth Day of June, 2016

Michelle K. Lee  
*Director of the United States Patent and Trademark Office*